United States Patent
Helfenbein et al.

(10) Patent No.: US 9,538,933 B2
(45) Date of Patent: Jan. 10, 2017

(54) QT INTERVAL MONITORING SYSTEM WITH ALARMS AND TRENDING

(75) Inventors: Eric Helfenbein, Sunnyside, CA (US); Sophia Huai Zhou, Camarillo, CA (US); James E. Lindauer, San Francisco, CA (US); Richard E Gregg, Westford, MA (US); Scott Kresge, West Newbury, MA (US); Bernd Wilm, Rohrdorf (DE); Kathryn A Egan, Derry, NH (US); Nancy Mutch, Amesbury, MA (US); Saeed Babaeizadeh, Camarillo, CA (US); Francis P Michaud, Hudson, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1905 days.

(21) Appl. No.: 12/676,948

(22) PCT Filed: Sep. 5, 2008

(86) PCT No.: PCT/IB2008/053609
§ 371 (c)(1),
(2), (4) Date: Jun. 21, 2010

(87) PCT Pub. No.: WO2009/034507
PCT Pub. Date: Mar. 19, 2009

(65) Prior Publication Data
US 2011/0092838 A1    Apr. 21, 2011

Related U.S. Application Data

(60) Provisional application No. 60/971,718, filed on Sep. 12, 2007.

(51) Int. Cl.
*A61B 5/0468* (2006.01)
*A61B 5/0452* (2006.01)

(52) U.S. Cl.
CPC ........... *A61B 5/0452* (2013.01); *A61B 5/0468* (2013.01)

(58) Field of Classification Search
USPC .................... 607/25; 600/515, 516, 518, 523
See application file for complete search history.

(56) References Cited

U.S. PATENT DOCUMENTS 3,759,248 A    9/1973  Valiquette
4,341,225 A *  7/1982  Gallant et al. ............... 600/523
(Continued)

FOREIGN PATENT DOCUMENTS

JP    H05237063 A    9/1993
JP    2004254930 A   9/2004
(Continued)

OTHER PUBLICATIONS

Helfenbein, E., et al., "An algorithm for continuous real-time QT interval monitoring," Journal of Electrocardiology, vol. 39, No. 4, Oct. 1, 2006, pp. S123-S127, XP005674486.
(Continued)

*Primary Examiner* — Eugene T Wu

(57) ABSTRACT

An ECG monitoring system continuously monitors a patient's ECG waveform and periodically identifies the patient's QT interval. QT interval values are averaged over time and a corrected interval value QTc and a change in QTc relative to a baseline, dQTc, are periodically produced. An alarm is responsive to updated QT interval values and issues an alarm whenever a selected QT value exceeds an alarm limit. The periodically produced QT interval values are stored and a trend display may be produced showing changes in the QT interval information over different periods of time. The trend display may selectively display the trend information either graphically or in tabular form.

12 Claims, 15 Drawing Sheets

(56) References Cited

U.S. PATENT DOCUMENTS

| | | | |
|---|---|---|---|
| 4,519,398 A * | 5/1985 | Lisiecki et al. | 600/523 |
| 4,977,899 A * | 12/1990 | Digby et al. | 600/515 |
| 5,560,368 A * | 10/1996 | Berger | 600/517 |
| 5,697,959 A * | 12/1997 | Poore | 607/32 |
| 6,324,423 B1 * | 11/2001 | Callahan et al. | 600/516 |
| 7,371,214 B2 | 5/2008 | Kouchi et al. | |
| 7,813,792 B2 * | 10/2010 | Xue et al. | 600/523 |
| 2004/0054294 A1 | 3/2004 | Ramseth | |
| 2004/0260192 A1 | 12/2004 | Yamamoto | |
| 2005/0246366 A1 * | 11/2005 | Kouchi et al. | 707/102 |
| 2008/0161708 A1 * | 7/2008 | Kenigsberg et al. | 600/516 |

FOREIGN PATENT DOCUMENTS

| | | |
|---|---|---|
| JP | 2007190228 A | 8/2007 |
| WO | 03/024323 A | 3/2003 |
| WO | 03/045224 A | 6/2003 |
| WO | 2004/098405 A | 11/2004 |

OTHER PUBLICATIONS

Bonate, P. L., "Rank power of metrics used to assess QTc interval prolongation by clinical trial simulation," Journal of Clinical Pharmacology, May 2000, vol. 40, No. 5, May 2000, pp. 468-474, XP002527971.

Jane, R., et al., "Evaluation of an automatic threshold based detector of wave form limits in Holter ECG with the WT database," Computers in Cardiology 1997, Lund, Sweden, Sep. 7-10, 1997, New York, NY, USA, IEEE, US, Sep. 7, 1997, pp. 295-298, XP010264514.

Helfenbein, E., et al., "An algorithm for QT intervals monitoring in neonatal intensive care units," Journal of Electrocardiology, vol. 40, No. 6, Nov. 12, 2007, pp. S103-S110, XP022347892.

"Table of Contents," Journal of Electrocardiology, ISCE 32nd Annual Conference, Apr. 32-26, 2007, vol. 40, No. 6, Nov. 2007, pp. A3-A5, XP002527976.

* cited by examiner

QT INTERVAL MONITORING SYSTEM WITH ALARMS AND TRENDING

This invention relates to monitoring systems which monitor heart signals and, in particular, to systems which monitor the QT interval of an ECG signal continuously in real time.

The QT interval is a measurement which can be taken on the electrocardiogram (ECG) waveform signal of human patients. The ECG is acquired by an electronic device (e.g., cardiograph, patient monitor, wireless telemetry device) with wires attached to temporary electrodes placed on the patient's limbs and torso. The ECG signal contains waveform components which, by standard, are labeled P-wave (atrial depolarization), QRS complex (ventricular depolarization), and T wave (ventricular repolarization). The QT interval is the time interval from the start of the QRS complex (ventricular depolarization) to the end of the T wave (end of ventricular repolarization).

The QT interval may become abnormally "prolonged" due to a number of causes such as genetic disposition, medication/drug induced side-effects, electrolyte imbalance. If the QT interval for a patient becomes prolonged, it is known that there is an increased risk of a potentially fatal arrhythmia (abnormal heart rhythm). This arrhythmia is called "torsade de pointes", and is a form of ventricular tachycardia (high rate). If this arrhythmia does not terminate on its own, or if the patient's heart rhythm is not returned to normal using a defibrillator, death will likely result.

The QT interval will change in a given patient in response to the patient's heart rate. Normally, if the heart rate increases, the QT interval will shorten; if the heart rate decreases, the QT interval will lengthen. Thus, it may be difficult to determine when the QT interval has become "prolonged" for a particular patient. To overcome this problem, any of a number of known heart rate correction formulas may be applied, which may be used on a measured QT interval at a measured heart rate to "correct" or normalize the QT interval measurement to what it would be if the heart rate was 60 beats-per-minute. The corrected QT Interval is commonly labeled "QTc". The correction formula developed by Bazett is commonly used in clinical practice. The QT Interval is corrected with this formula by dividing the measured QT interval by the square root of the observed beat-to-beat (R-R) interval, measured in seconds. Another correction formula that may be used was developed by Fridericia, which divides the QT interval by the cube root of the beat-to-beat interval. It is thus the QTc interval which is commonly computed to determine if there is abnormal QT interval prolongation for a patient. A QTc value may be considered prolonged if greater than 470 milliseconds in males and greater than 480 milliseconds in females. As a general rule, if a patient's QTc interval exceeds 500 milliseconds, or if there is an observed QTc increase greater than 60 milliseconds (e.g., after start of the administration of a medication), the QTc is considered dangerously "prolonged".

Because a number of medications are known to cause a QT prolongation (a potentially proarrhythmic drug), the U.S. Food and Drug Administration requires that all medications be tested to determine if they have the potential to prolong the QT interval. Pharmaceutical companies or contract research organizations (CROs) routinely collect ECGs using cardiographs or Holter monitoring devices and measure the QTc intervals on subjects enrolled in drug clinical trials.

In the hospital setting, surveillance of the QT interval is also important, since many hospital patients are taking medications which may have proarrhythmic effects, or may be experiencing electrolyte imbalances which may cause the QT interval to become prolonged, or may be affected by combinations of factors. These situations have been addressed by the writing group for the American Heart Association (AHA), which has published a scientific statement to endorse a practice standard for ECG monitoring of patients in the hospital clinical setting. For the first time in ECG monitoring practice, this guidance includes a recommendation for QT interval monitoring for patients on potentially proarrhythmic drugs. In addition, the American Association of Critical Care Nurses (AACN) has issued a practice alert that specifically addresses the need for surveillance of the QT interval.

The AHA scientific statement provides suggestions for how the QT interval may be measured manually, and suggests that the QTc can be documented "by using a rhythm strip example before the drug is initiated and thereafter at least every eight hours." Hospitals that follow the AHA practice standard usually have a protocol for QT interval monitoring that requires one QT interval measurement from each patient every four to eight hours. The clinical staff usually does this by printing an ECG strip with a single ECG lead and manually measuring the QT interval on one beat on this one lead. Some monitoring systems have electronic caliper capability to assist the clinician in performing the manual QT interval determination. The Bazett correction formula is then used to calculate QTc based on a single (and often the preceding) R-R interval. However, infrequent manual measurements of the QT interval is problematic. In our paper entitled "An algorithm for continuous real-time QT interval monitoring," *J. Electrocardiology* vol. 39 (2006) at pp S123-S127, we analyzed the beat-to-beat variability in manual annotations by cardiologists of QT intervals of the PhysioNet QT database. The results of this analysis revealed that the mean QT range of one QT interval manually annotated by several physicians was 76 msec., and the median was 68 msec. The case with the least amount of variation had a range of 24 msec. and the worst case had a variation of 236 msec. This high variation is believed to be due to beat-to-beat QT variability and manual measurement error. The high variation implies that a randomly selected beat will not be representative, and that the amount of normal variation and/or measurement error is greater than the QT prolongation that the clinical staff is attempting to detect, usually 60 msec.

Accordingly it would be desirable to have an automated system for measuring the QT interval that eliminates manual measuring errors.

It is further desirable to have an automated system that will remove beat-to-beat QT variability and provides stable QTc measurements while tracking slowly changing QTc prolongations as they occur in real time, rather than retrospectively reviewing changes that occurred over many previous hours.

In accordance with the principles of the present invention, a patient monitoring system is described which monitors a patient's QT interval over time. The monitoring system includes one or more adjustable alarm limits which trigger an alarm when the duration of the QTc interval and/or an increase of the QTc interval is beyond an acceptable level. In accordance with a further aspect of the present invention, the trend of the QTc interval duration is recorded over time for review by a clinician.

DETAILED DESCRIPTION

Figure 1:
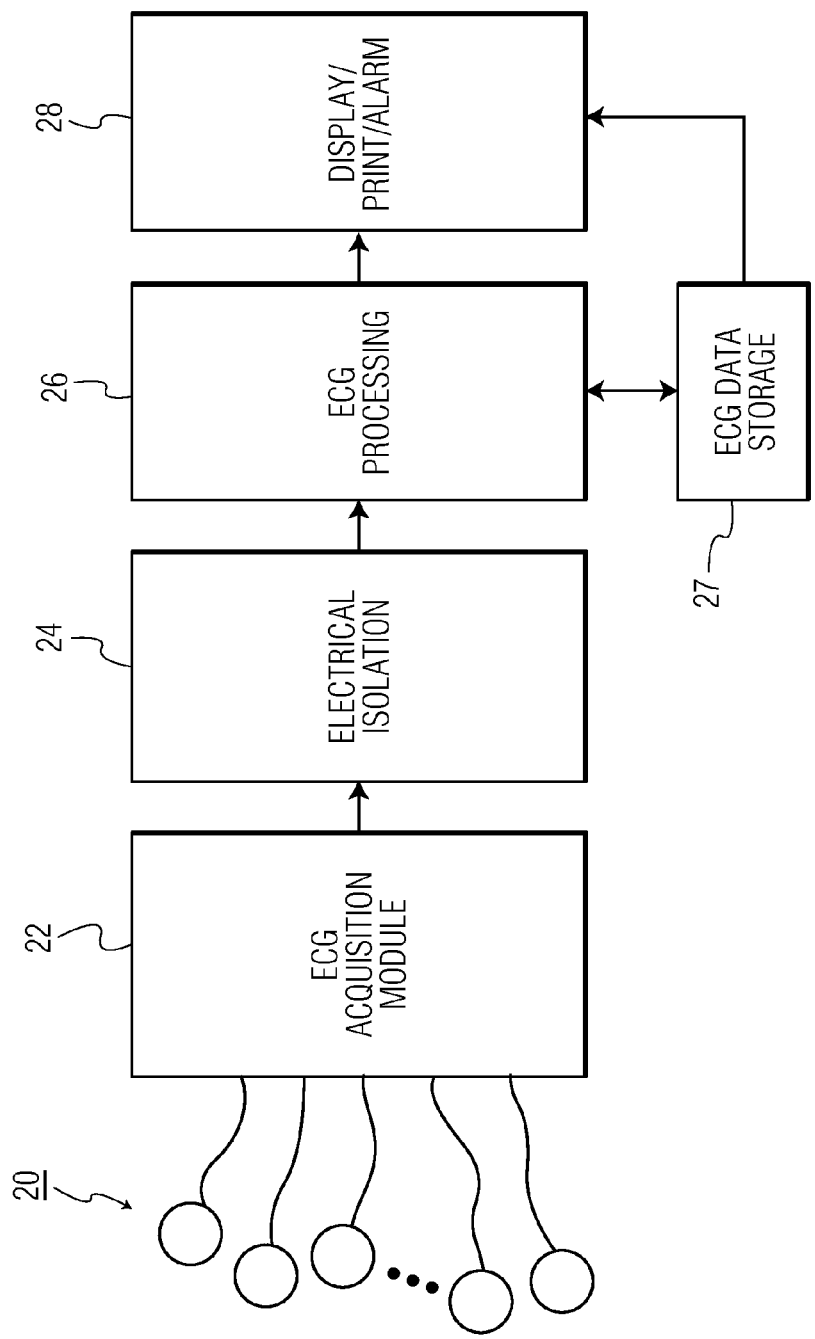
FIG. 1 illustrates in block diagram form the major elements of an ECG monitoring system.

FIG. 1 illustrates in block diagram form a ECG system suitable for the acquisition of ECG data for QT interval monitoring in accordance with the present invention. A plurality of electrodes 20 are provided for attaching to the skin of a patient. Usually the electrodes are disposable conductors with a conductive adhesive gel surface that sticks to the skin. Each conductor has a snap or tab that snaps or clips onto an electrode wire of the ECG system. The electrodes 20 are coupled to an ECG acquisition module 22 that preconditions the signals received by the electrodes. This preconditioning generally includes amplification and digitizing of the body's electrical signals received by the electrodes. The electrode signals are coupled to an ECG processing module 26, generally by means of an electrical isolation arrangement 24 that protects the patient from shock hazards and also protects the ECG system when the patient is undergoing defibrillation, for instance. Optical isolators are generally used for electrical isolation. The processed ECG information is digitally stored in an ECG data storage device 27 and the current or previously stored ECG data may be displayed on an image display or printed in an ECG report by an output device 28, which is also suitable for triggering alarms as described below.

Figure 2:
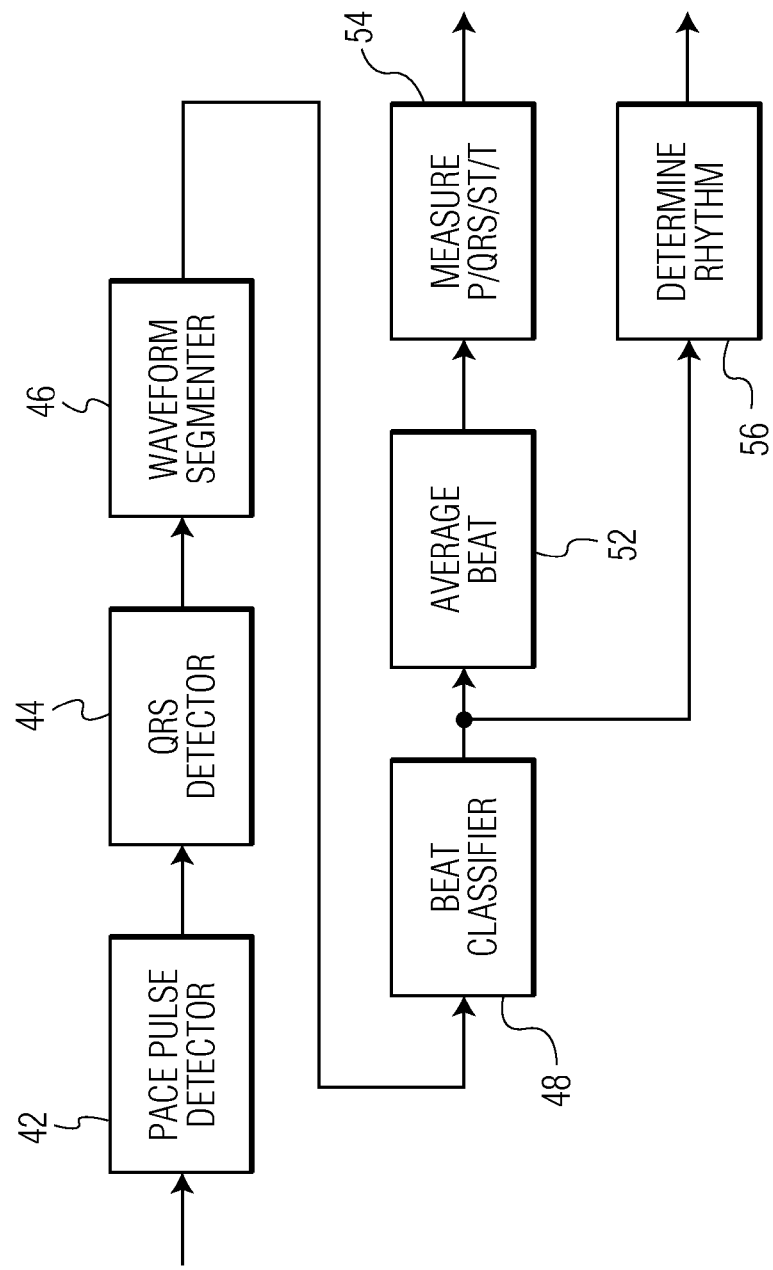
FIG. 2 illustrates in block diagram form the ECG waveform processing portion of the ECG monitoring system of FIG. 1.
Figure 3:
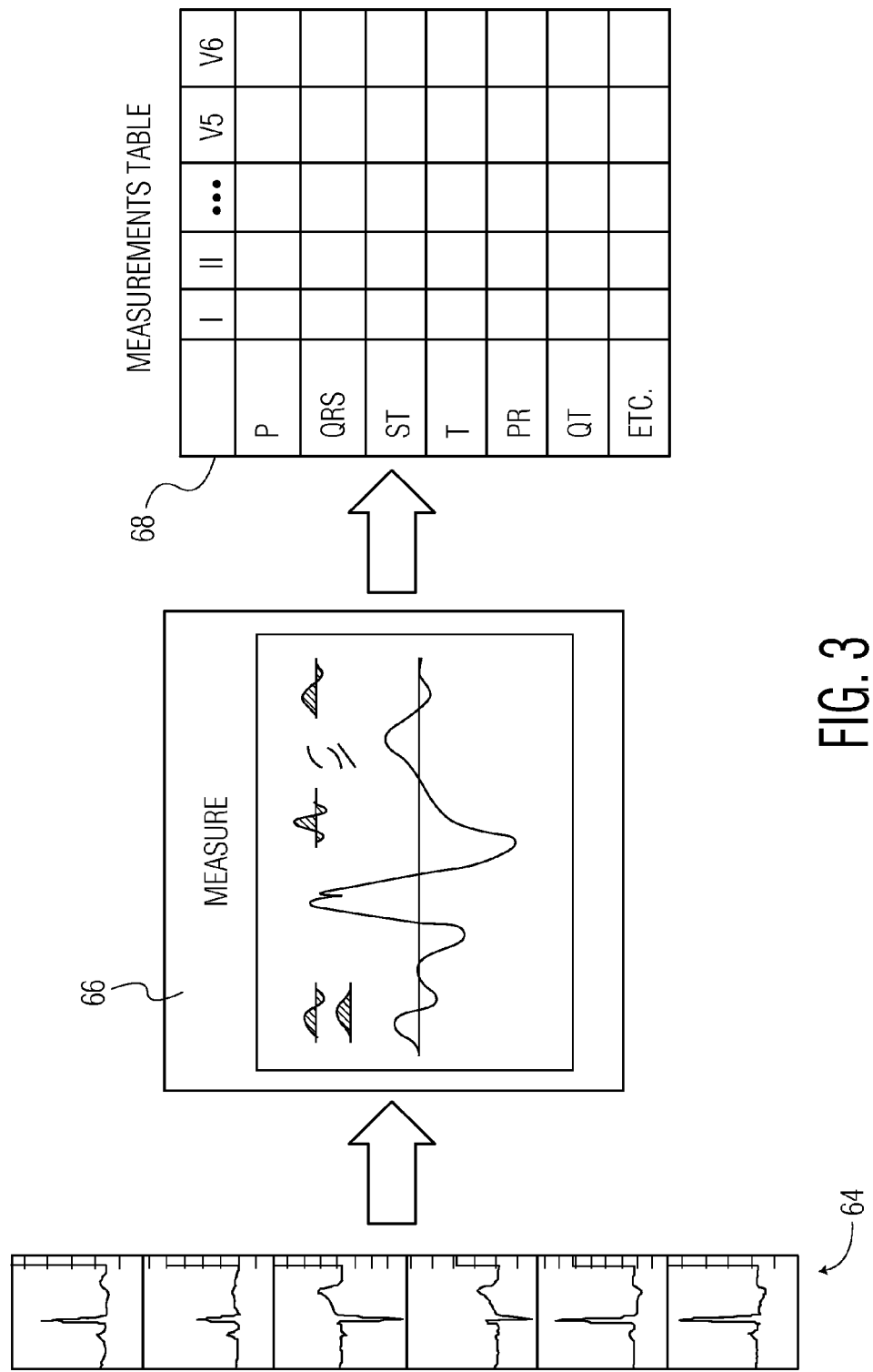
FIG. 3 illustrates the types of measurements which may be made by the ECG monitoring system of FIG. 1.

FIG. 2 is a block diagram of the processing or analysis portion of a typical monitoring ECG system. A pace pulse detector 42 identifies and sets aside electrical spikes and other electrical abnormalities produced by a pacemaker for patients who are wearing one. A QRS detector 44 detects the dominant pulse of the electrical traces. The Q-R-S segments of an ECG waveform or trace delineate the major electrical pulse of the trace, which is the pulse that stimulates a contraction of the ventricles. Delineation of the QRS complex forms the basis for detecting the lesser perturbations of the trace, which is performed by the waveform segmenter 46. The waveform segmenter delineates the full sequence of trace segments including the P wave and the Q to T segments of the ECG trace. With each waveform now fully delineated, a beat classifier 48 compares each new beat with previous beats and classifies beats as normal (regular) for the individual or abnormal (ectopic). The classification of the beats enables an average beat analyzer 52 to define the characteristics of a normal heartbeat and the amplitudes and segment durations of an average beat are measured at 54. The beat classifications are used to determine the heart rhythm at 56. FIG. 3 is a functional illustration of a portion of this ECG trace processing. In FIG. 3 the average beat traces 64 of the leads are measured for various characteristics shown at 66, such as the amplitudes and durations of the Q wave, the R wave, and the T wave and inter-wave intervals such as QRS and QT. The measurements are illustrated as recorded in a measurement table 68.

While a QT monitoring system of the present invention may be implemented in a cardiograph or diagnostic ECG system, preferably it is implemented in a patient monitoring system such as the IntelliVue patient monitor available from Philips Medical Systems of Andover, Mass., which incorporates the ECG functionality described above. The monitoring system may be composed of a single bedside monitor, or may consist of a plurality of bedside monitors connected to what is commonly referred to as a monitoring central station. The monitoring system may also be comprised of wearable telemetry ECG devices which transmit the ECG signal to an antenna network connected to the central monitoring station, so that patients may be ambulatory within the hospital while they are being monitored. The present invention may also be embodied in Holter monitors whereby QT interval monitoring can be performed on an outpatient basis.

Figure 4:
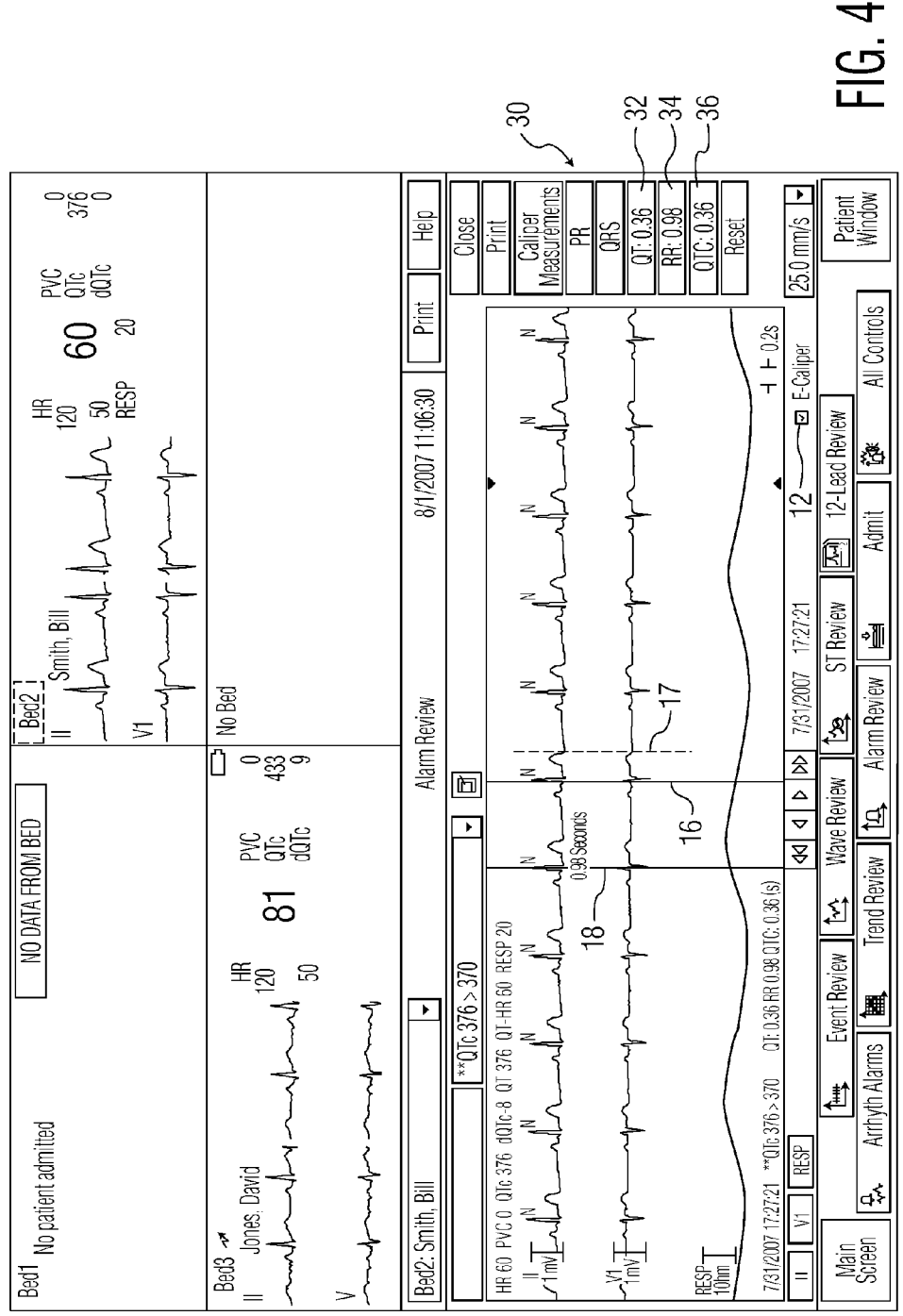
FIG. 4 illustrates the display screen of an ECG monitoring system by which a clinician may manually measure the QT interval of an ECG waveform.

FIG. 4 illustrates the display screen of a patient monitoring system adapted for manual measurement of the QT interval. At the top of the display screen are areas for the display of patient data from the patients assigned to four beds in a hospital, Bed1, Bed2, Bed3, and Bed4. The latter is unoccupied and shows up as "No Bed" on the display. When a patient is ambulatory and is wearing a wireless monitor, a lightning bolt-like icon is displayed next to the bed number as is the case for Bed3 in this example. In this example an ECG strip 14 has been recorded for the hypothetical patient in Bed2, Bill Smith, and a measurement is made of patient Smith's QT interval. The display screen of FIG. 4 shows a feature called "E-Caliper" which assists the physician or nurse in making the QT interval measurement. As mentioned above, the current practice is to capture an ECG trace and measure the patient's QT interval every four to eight hours. The ECG strip 14 has a number of heartbeats in which the QT interval may be measured. The clinician turns on the E-Caliper feature by checking the box 12 near the bottom of the display. A list of caliper measurement boxes 30 then appears at the right side of the screen and a measurement cursor 16 appears over the ECG trace. The clinician uses a mouse or other pointing device to move the cursor 16 horizontally until it is aligned with the Q point of a heartbeat as shown in FIG. 4. The clinician clicks the pointing device and a second cursor appears, which the clinician positions horizontally at the T point of the heartbeat as indicated by dashed line 17. When the clinician is satisfied with the positions of both cursors the QT box 32 at the right side of the screen is clicked and the interval between the two cursors is measured and appears in the QT box 32, which in this example is 0.36 seconds. The clinician then positions a third cursor at the Q point of the previous heartbeat as shown by cursor 18. The interval between cursors 18 and 16 thus specifies the R-R interval of the previous heartbeat, which is used for heart rate correction. When the cursors are positioned as shown in FIG. 4, the clinician clicks the RR box 34 and the R-R interval is measured and displayed, which is 0.98 seconds in this example. The measured QT interval is then corrected for the heart rate of the patient (the R-R interval of the previous heartbeat), and the resulting QTc value is displayed in box 36. The clinician now has a corrected QTc value to compare with the previous measurement of four or eight hours earlier and can see if there has been any prolongation of the QT interval over that period, at least to the extent that it is revealed by these measurements.

In accordance with the principles of the present invention the QT interval of a patient is continuously monitored in real time. An alarm alerts a caregiver if a QT parameter such as the QTc exceeds a desired limit. In a preferred embodiment the patient's ECG is continuous monitored, typically by a multi-lead (usually 7 or 8 lead) ECG system in the hospital setting. The ECG system acquires the ECG waveform of each heartbeat at each electrode. The lead signals are computed and all of the heartbeats at each lead are averaged to develop an average signal for that lead. This can be done with or without beat classification. All of the lead signals are then combined by computing an RMS signal. For each ECG sample the squares of each representative complex from all available leads are summed, divided by the number of leads, and the square root is taken of the result. This produces a representative beat for a minute of time. The QT interval is then measured by identifying the Q onset and the T offset. This may be done using a slope-intercept technique, the Swatzell technique, or other appropriate process. The QT interval for the minute is corrected using one of the correction algorithms to produce a QTc value for the minute.

This process is repeated every minute to accumulate five such measurements every five minutes. The five measurements are then used to produce a single set of measurements for the five minute period. While a mean or average value could be computed or some other aggregation used, in the preferred embodiment the median value of the QTc interval and the corresponding QT value are selected as the representative values for the five minute period. The QT monitoring system continues in this manner to produce updated values every five minutes.

When the QT monitoring system is initially turned on, each new one minute value is displayed as it is produced. After the first five minutes of operation the five sets of values necessary for a five minute measurement have be accumulated and a set of five minute values is displayed. Thereafter these values are updated every five minutes.

Figure 5:
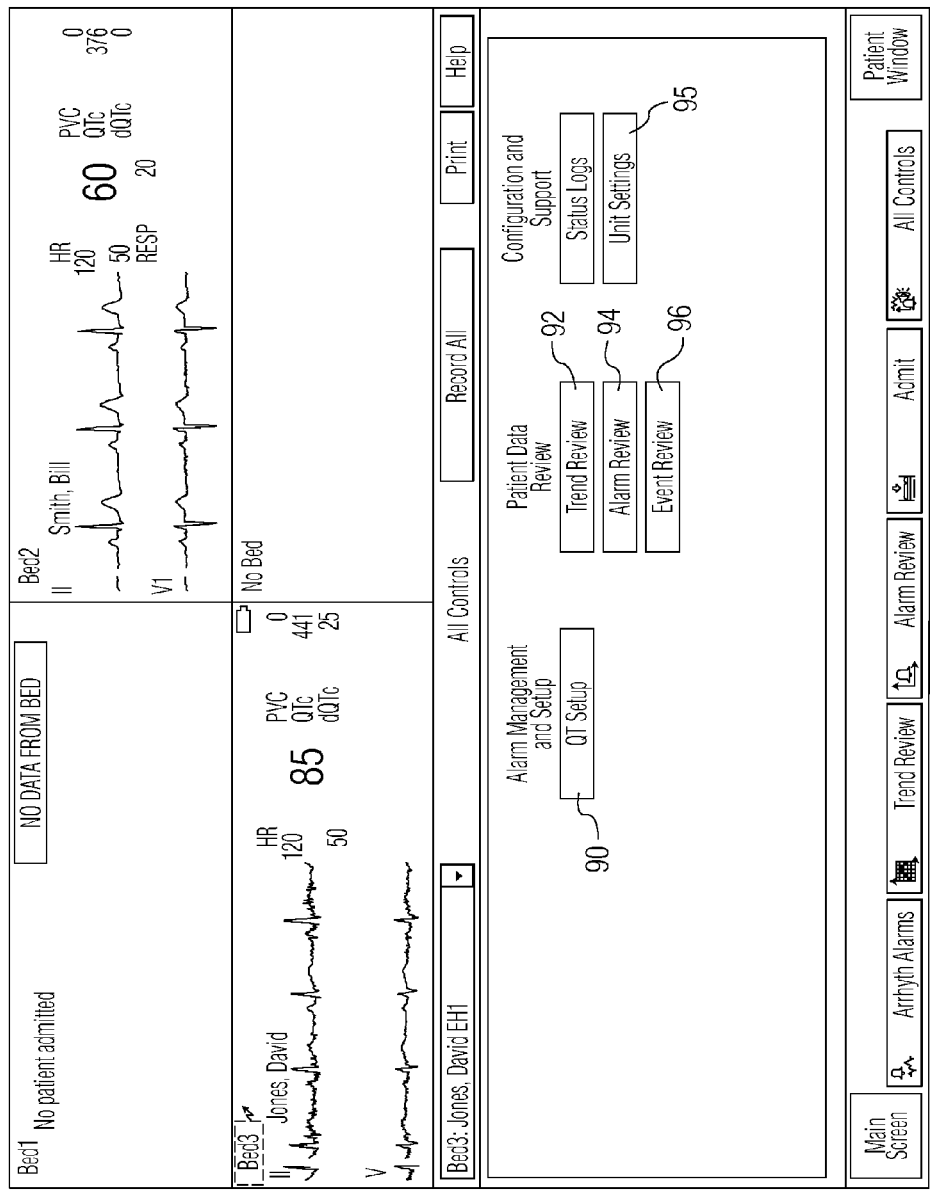
FIG. 5 illustrates the control screen of a patient monitoring system of the present invention.

FIG. 5 shows a control screen of a patient monitoring system constructed in accordance with the principles of the present invention. The lower half of the display screen contains a variety of control buttons for different monitoring and diagnostic tasks which can be performed by an ECG monitoring device. Particular to QT monitoring in accordance with the present invention are the QT Setup button 90 which accesses the QT setup screen of FIG. 6 below, and the Trend Review button 92, the Alarm Review button, 94, and the Event Review button 96 which access display screens as described in subsequent drawing figures.

Figure 6:
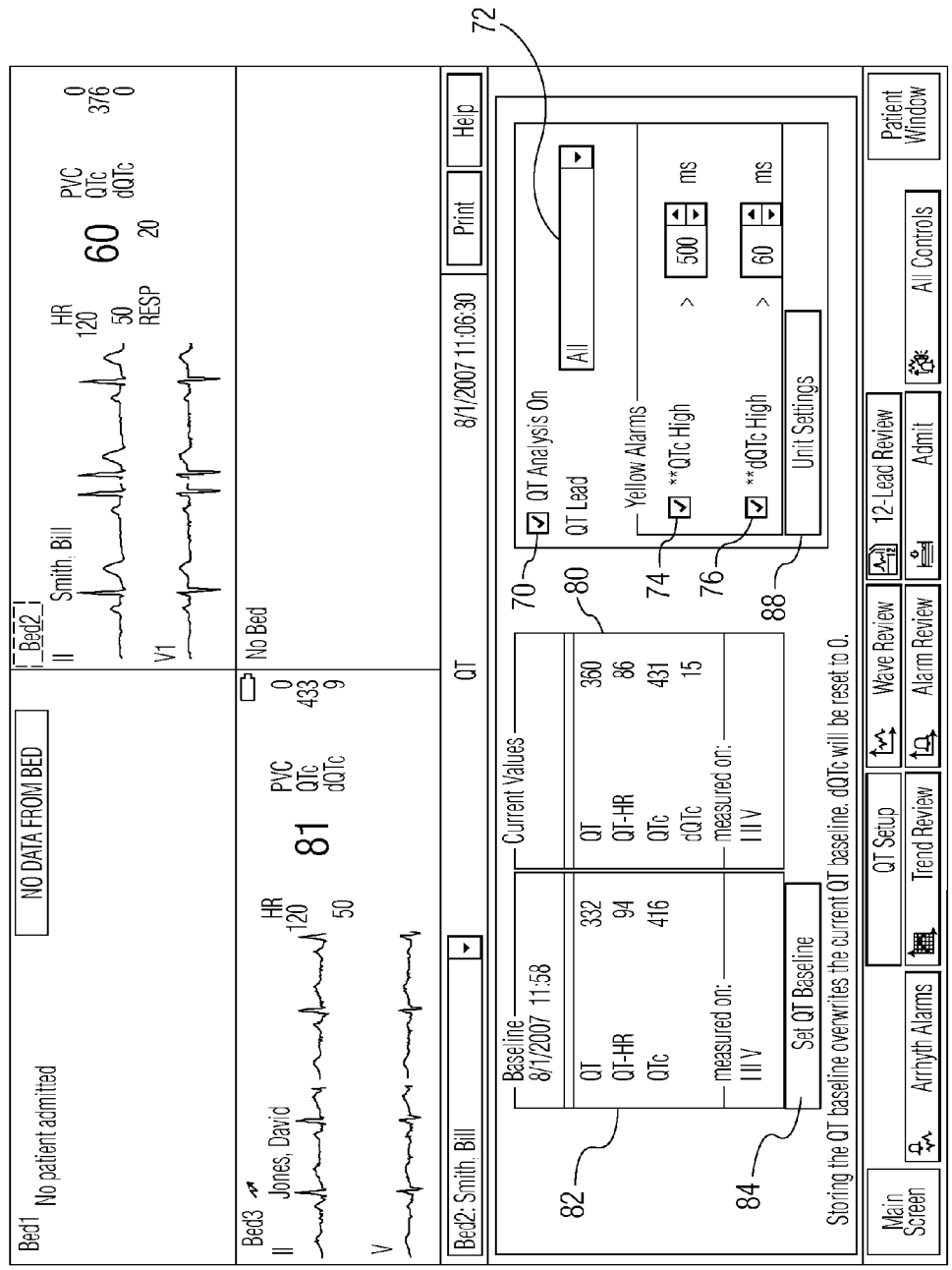
FIG. 6 illustrates the QT interval monitoring setup screen of a patient monitoring system constructed in accordance with the principles of the present invention.

FIG. 6 shows a setup screen for QT monitoring, which is accessed by pressing the QT Setup button in FIG. 5. As indicated in the middle of the screen this display is of the setup values for patient "Bill Smith" in Bed2. Multiple patients can undergo QT monitoring at the same time from a central station for patient monitoring, to which all of the ECGs for the monitored patients are reported. The QT monitoring setup values are shown in the lower half of the screen. A box 70 for "QT Analysis On" is checked when Bill Smith's ECG is monitored for QT prolongation. Below this line is a box 72 identifying the ECG leads which are used for QT analysis. At this time all ECG leads are used in the analysis. Below this line is the alarm limit box for QTc and dQTc, the corrected QT interval measurement and the change in the corrected QT interval relative to a baseline QTc interval. A box 74 is checked to turn on an alarm for QTc. The alarm for QTc in this example is turned on with an alarm setting of 500 msec. This will cause an alarm to sound at the central station if the patient's QTc measurement exceeds 500 msec. As previously mentioned, if a patient's QTc interval exceeds 500 milliseconds after start of the administration of a medication, the QTc is considered dangerously prolonged. QTc values in the range of 470-480 msec are considered to be prolonged by some standards, which would prompt a lower alarm setting. The alarm setting of 500 msec can be changed by clicking on the up and down carats to the right of the box containing the setting. Similarly, a box 76 is checked to turn on an alarm for dQTc. In the example shown the dQTc alarm level has been set at 60 msec.

Figure 8:
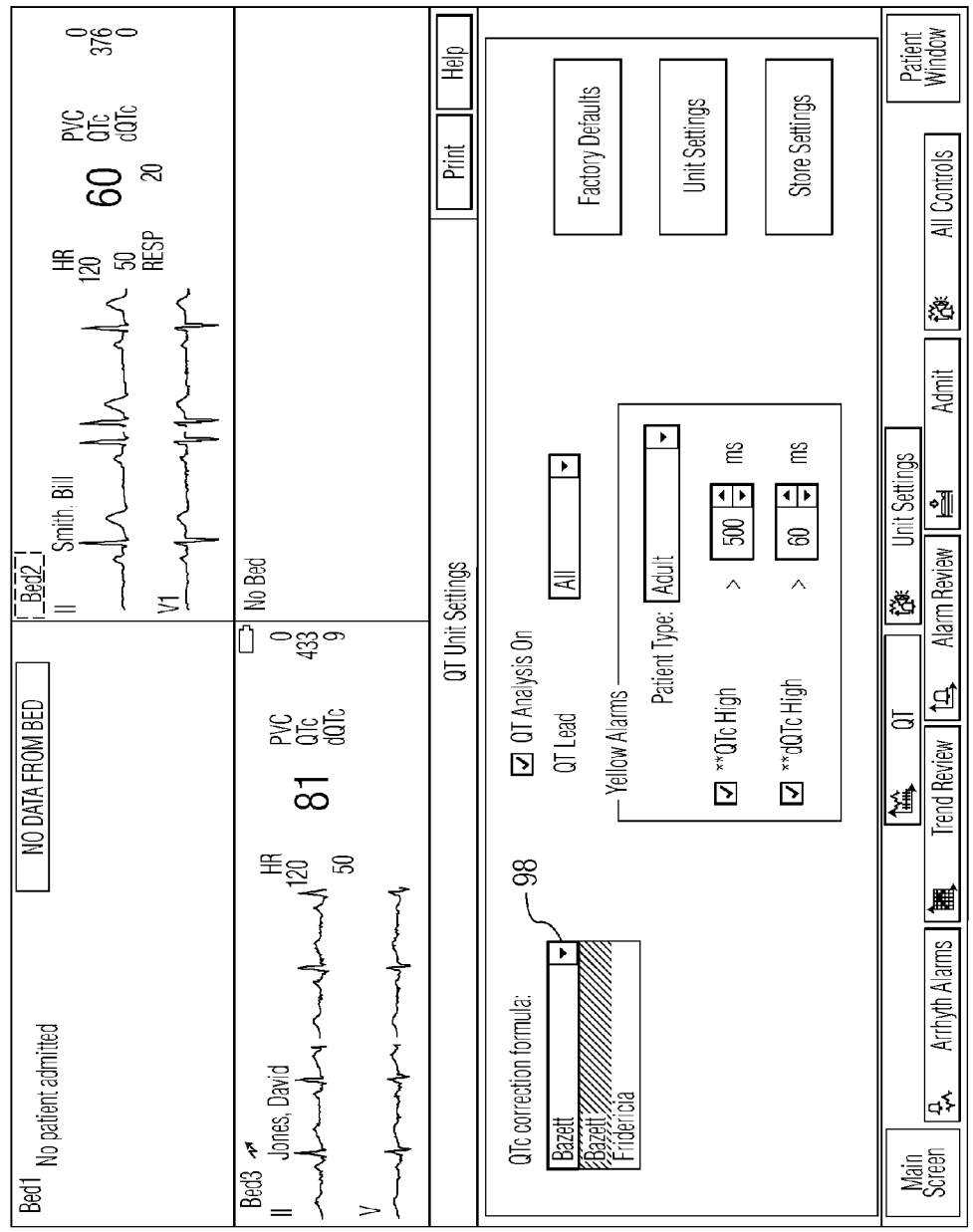
FIG. 8 illustrates the correction formula and alarm limit setup screen of a QT interval monitoring system of the present invention.

Below the Alarm setting box on the display is a button 88 called Unit Settings, which sets the alarm limits to those configured in the Unit Settings. The User Settings setup is accessed by the Unit Settings button 95 in FIG. 5 (All Controls). The Unit Settings button 95 takes the user to a setup screen for the type of correction to be employed in calculating QTc. This display screen is shown in FIG. 8 which is described below.

On the left side of the QT setup screen are a Baseline box 82 and a Current Values box 80. The Current Values box 80 shows the values of the QT interval, the heart rate (QT-HR), QTc and dQTc which were calculated for the previously completed five minute time period as described above. At the start of QT monitoring the previous period is only one minute until a full five minute period is completed. At the bottom of the box is a list of the leads used in the computation of those values. In this example leads I, II, and V were used to compute the current values. A clinician observing the QT setup screen would see the Current Values updated every five minutes after the startup period of QT monitoring.

The box 82 to the left shows the Baseline values that are used for determining dQTc. Since dQTc is an increase relative to a baseline, the baseline used is shown in this box 82. Initially the Baseline values are those of the first five minute analysis period. These Baseline values can be changed at any time to the Current Values by clicking on the "Set QT Baseline" button 84, which causes the Current Values to appear in the Baseline box 82 and become the new Baseline values. In the illustrated example the baseline QTc value is 416 msec and the dQTc alarm setting is 60 msec., meaning that the dQTc alarm will issue if QTc exceeds 476 msec (416+60). This example shows that the Current Value for QTc is 431 msec which, as the dQTc value immediately below indicates, is a dQTc increase of 15 msec over the baseline QTc value of 416 msec. Clicking on the "Set QT Baseline" button 84 with the screen values shown would cause the new baseline QTc value to become 431 msec.

Figure 7:
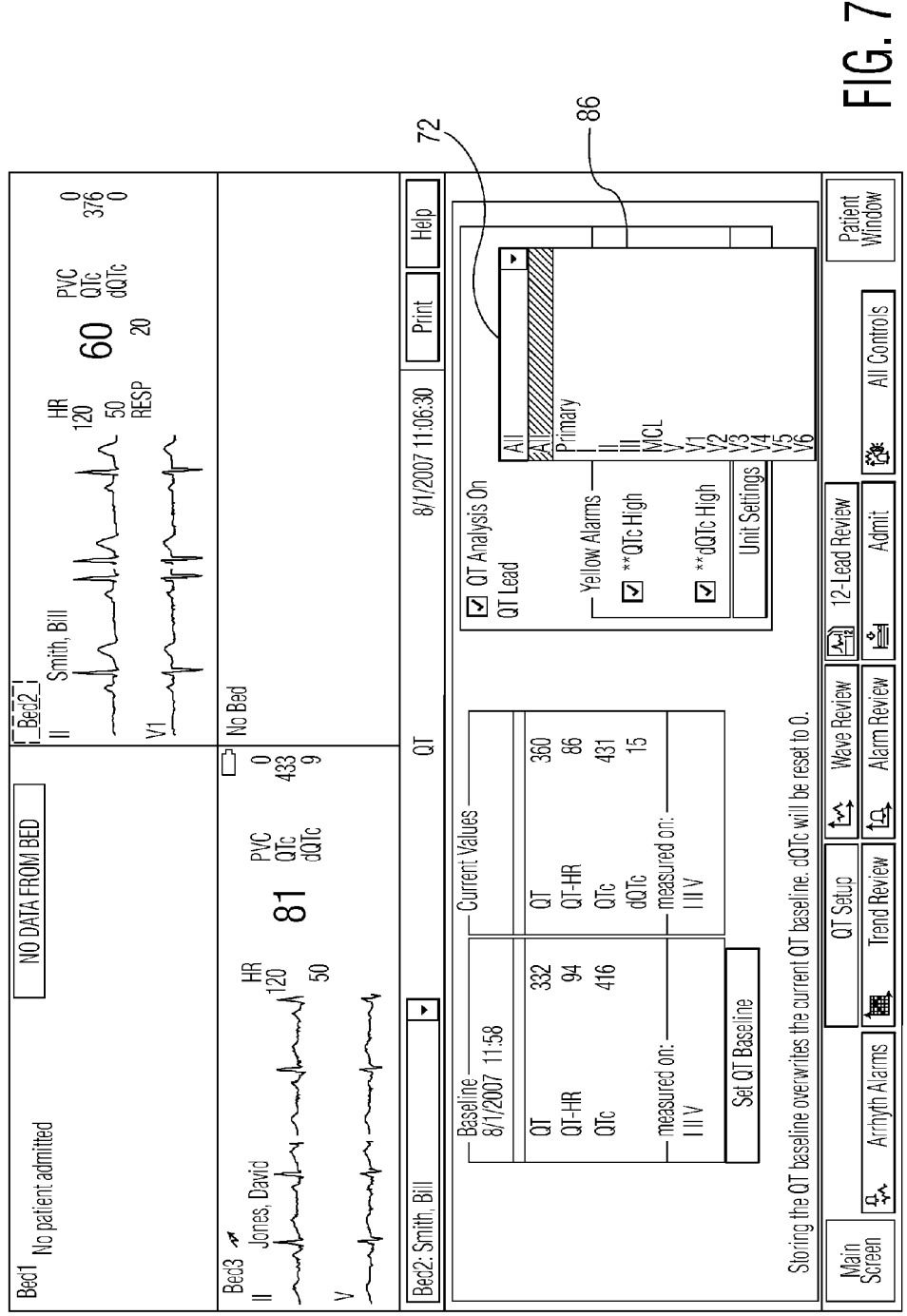
FIG. 7 illustrates the lead selection setup screen of a QT interval monitoring system of the present invention.

FIG. 7 shows the QT setup screen when the user pulls down the menu 86 for lead selection. In this example the user can select the signals from all leads to be used in the measurement of the QT interval, the primary lead, or another one of the individual leads of the ECG. The user clicks on a selection to cause the selected lead or lead group to appear in the lead box 72.

FIG. 8 shows the QT Unit Settings display screen that appears when the user clicks the "Unit Settings" button 95 on the setup screen of FIG. 5. In this example the QT Unit Settings screen shows that QT analysis is turned on, that all of the ECG leads are being used for QT analysis, and that the alarms for both QTc and dQTc are set. This screen also shows a pull-down menu 98 by which the user can select the correction formula for the QTc correction. In this example the user can select either the Bazett or the Fridericia correction formula.

Figure 9:
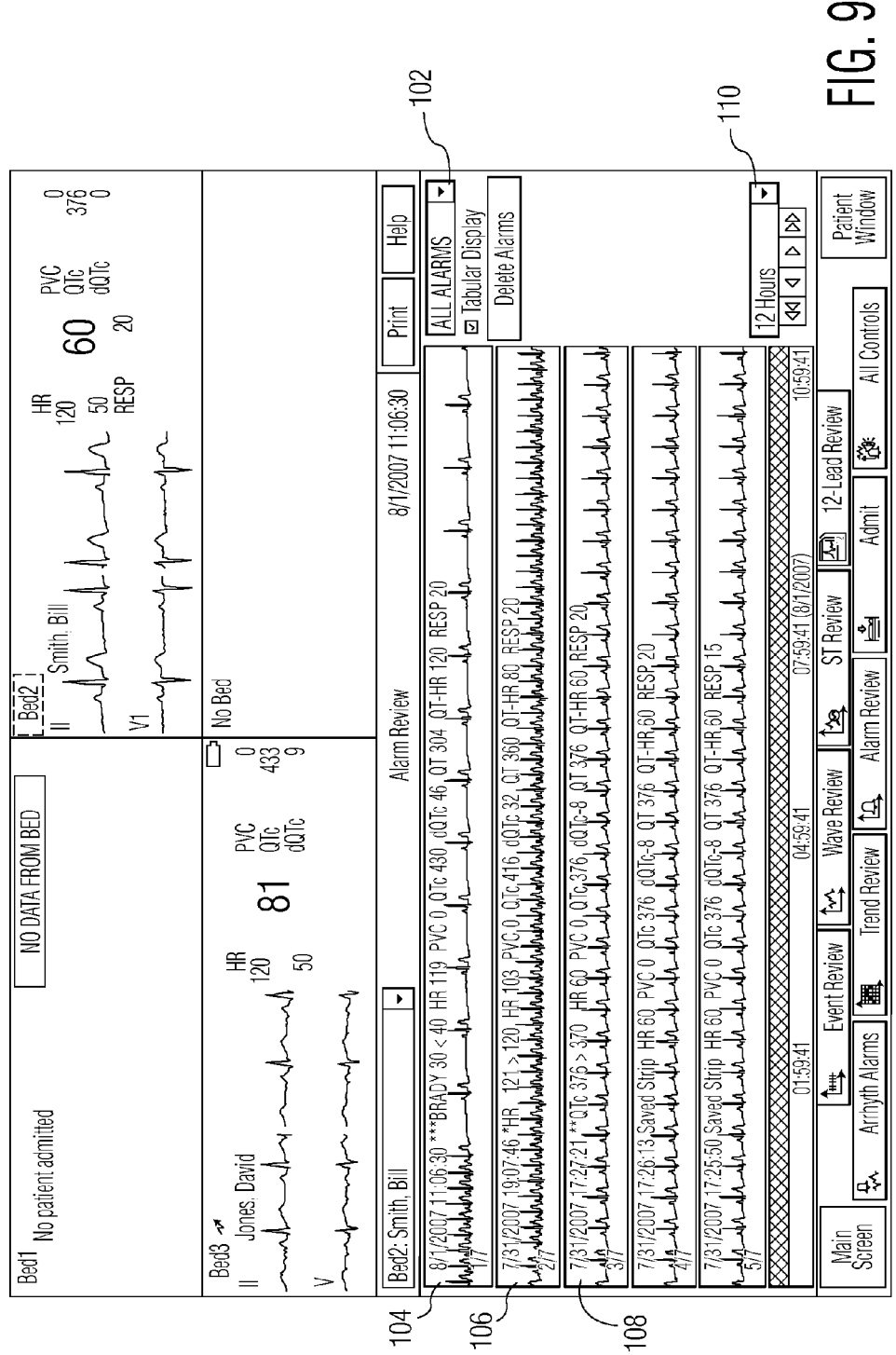
FIG. 9 illustrates the alarm review and list of alarms screen of a QT interval monitoring system of the present invention.

When the Alarm Review button 100 at the bottom of the screen is clicked, the user can review all of the ECG strips that were saved when an alarm for a monitored ECG condition occurred. An example of such ECG alarm strips for patient Bill Smith in Bed2 is shown in FIG. 9. In this example "ALL ALARMS" were selected using the pull-down menu at the right side of the screen, displaying three strips saved during alarm conditions and two other strips that were saved manually by a clinician. The first strip 104 was saved when the patient exhibited a bradycardia (low heart rate) condition at 11:06:30 on Aug. 1, 2007. As the notation above the strip indicates, this alarm occurred because the patient's heart rate dropped to 30 beats per minute, exceeding the alarm setting of less than 40 beats per minute. The next strip 106 shows an alarm that occurred because the patient's heart rate exceeded the alarm setting of greater than 120 beats per minute. The third strip 108 was saved because the patient's QTc interval exceeded the alarm setting of 370 msec. Thus it is seen that a clinician can review the graphical ECG waveform for a monitored patient after an alarm event occurs by recalling the ECG strips automatically saved at the time of an event, even if the alarm condition was not immediately noticed at the central monitoring station. In this example all of the alarm conditions which occurred for a patient during the previous twelve hour time period are reviewed by selecting "12 Hours" in the menu box 110 at the lower right side of the screen.

Figure 10:
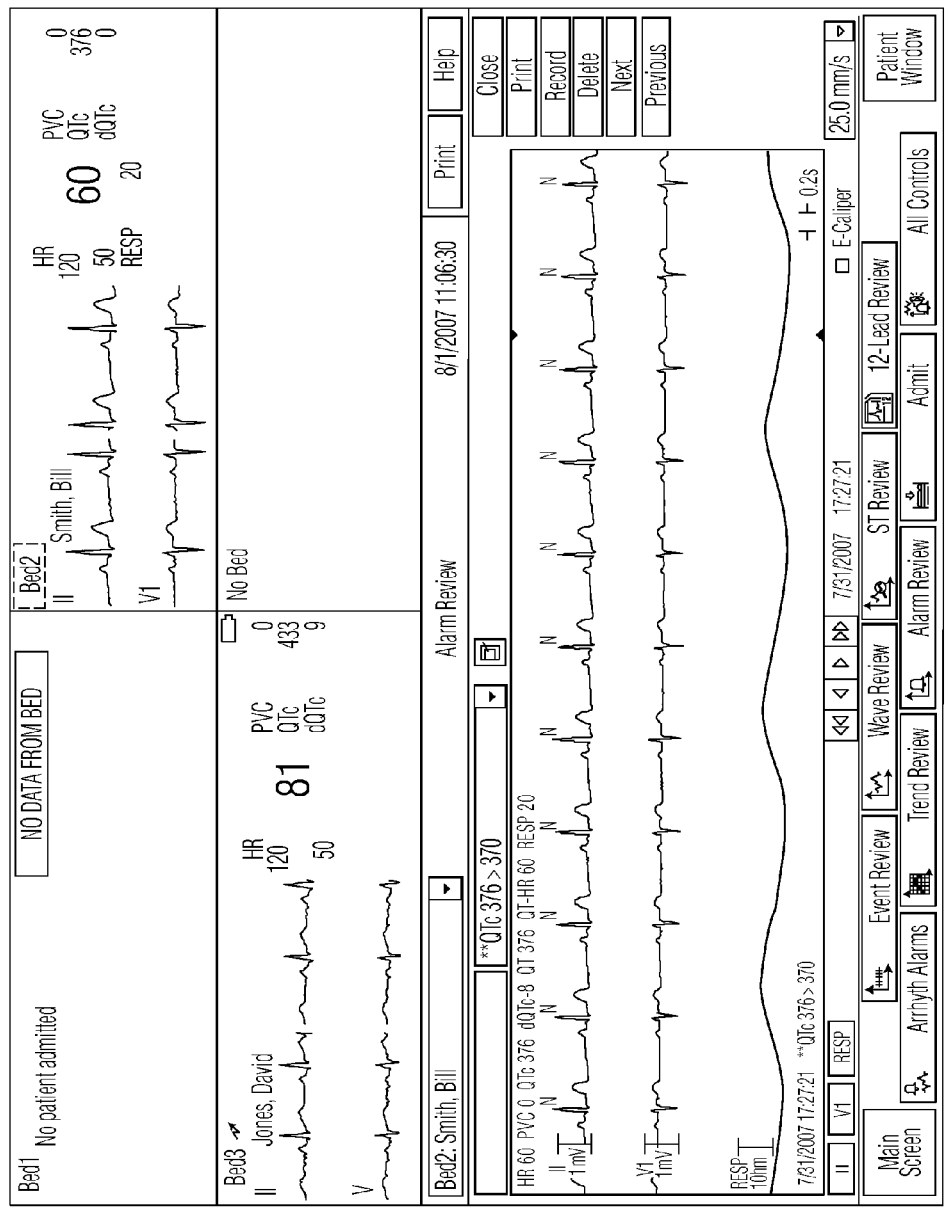
FIG. 10 illustrates an alarm review screen of a QT interval monitoring system of the present invention which shows the review of a single alarm strip.
Figure 11:
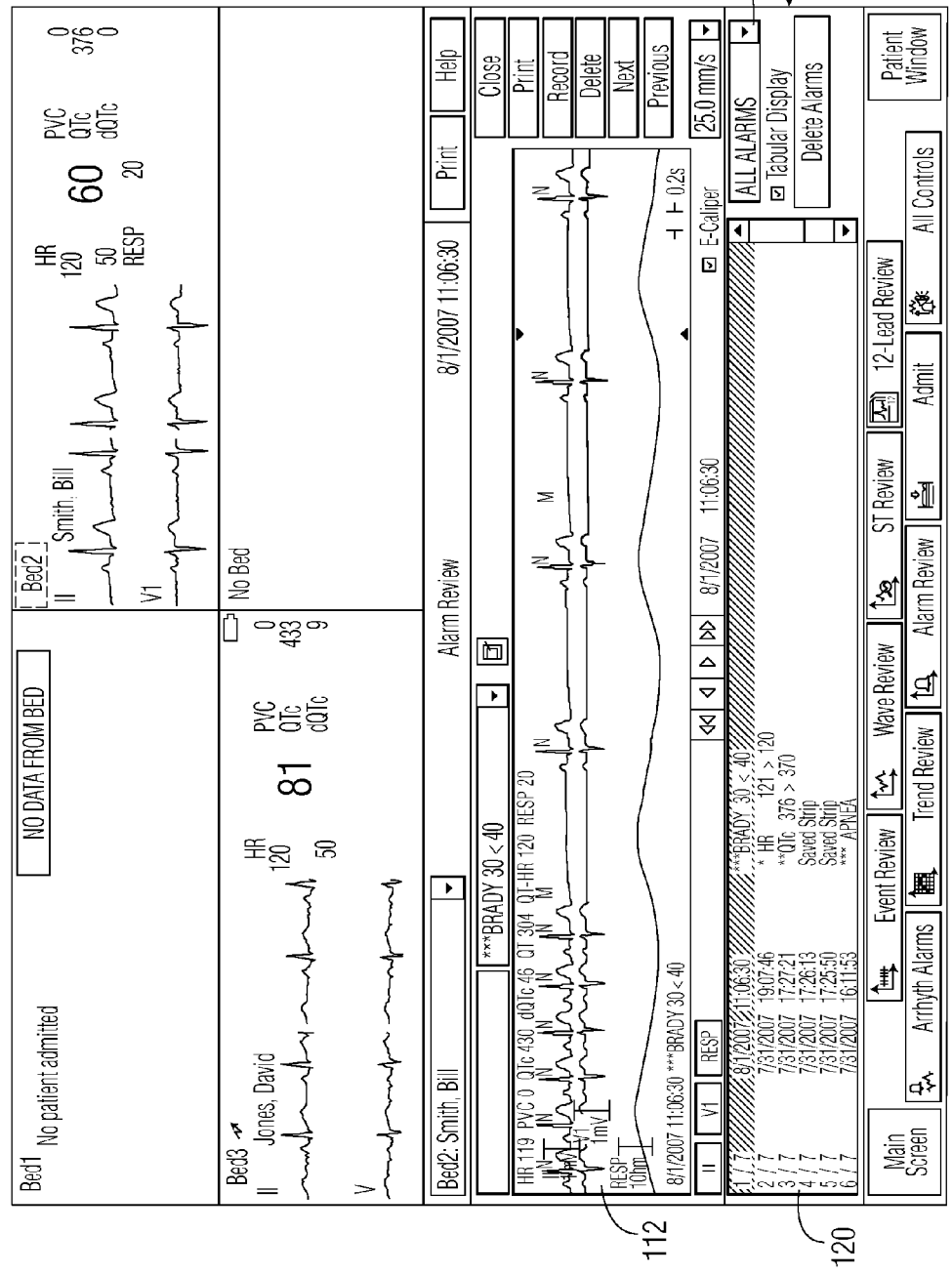
FIG. 11 illustrates an alarm review screen of a QT interval monitoring system of the present invention which shows alarm information both graphically and in tabular form.

If a clinician wants to see an alarm strip in greater detail, and also other monitored conditions of the patient at the time of the alarm, the clinician can select one of the alarm strips for detailed review as shown in FIG. 10. In this example the clinician has chosen to review the patient's bodily functions at the time that the QTc interval was prolonged to 376 msec., above the alarm limit of 370 msec. In the example of FIG. 10 the stored ECG strips show the ECG waveforms for leads II and V1 at the time of the alarm, as well as the patient's respiration. FIG. 11 shows the display screen with a detailed display of the patient's bodily functions at the time of the bradycardia condition in box 112 of the screen, and a tabular list of all of the patient's alarms in box 120. The tabular list of all of the alarms is selected by selecting "ALL ALARMS" in the pull down menu 102 and the "Tabular Display" checkbox in line 122 of the screen.

Figure 12:
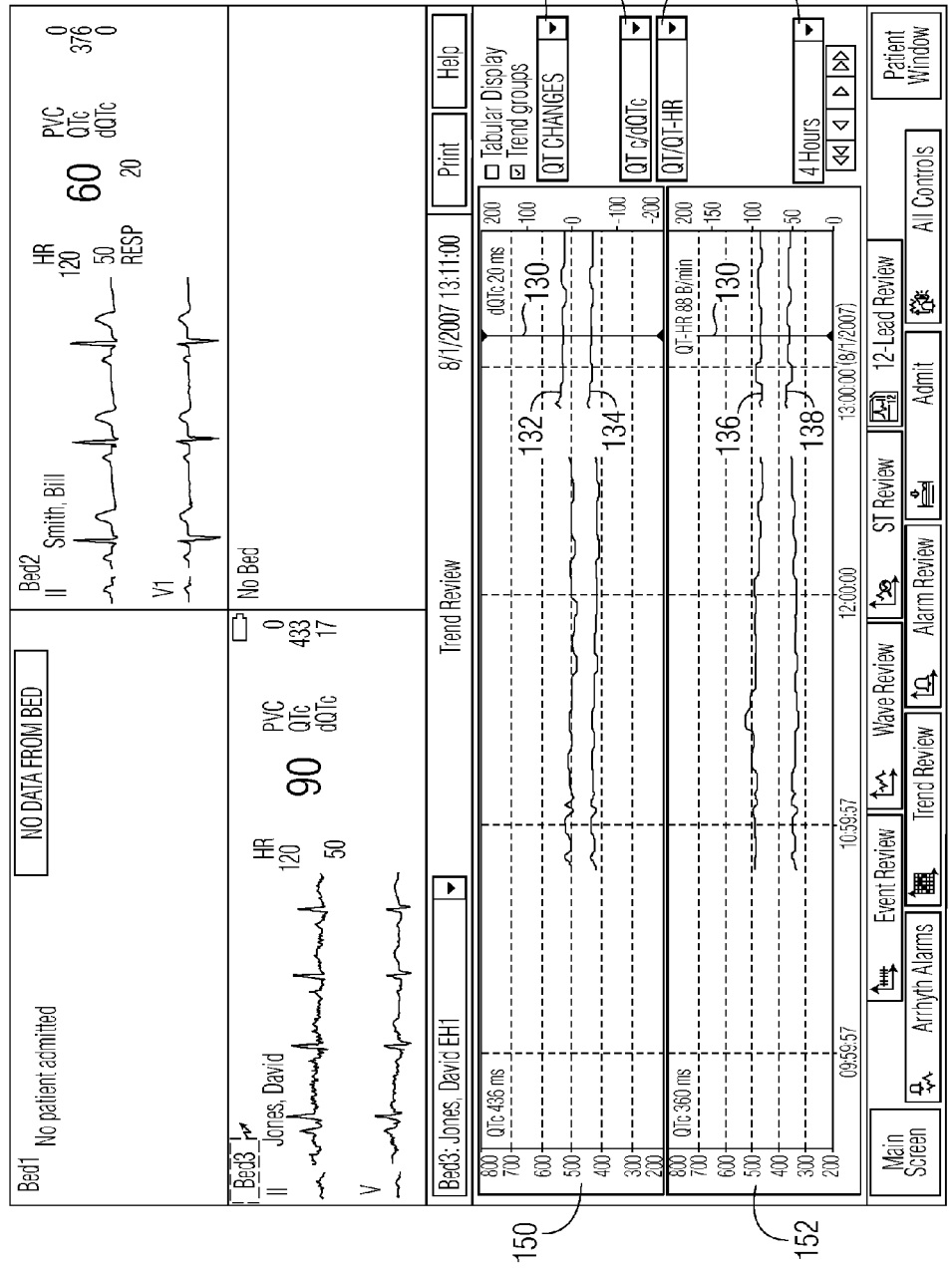
FIG. 12 illustrates a screen of a patient monitoring system displaying the trend of the QT interval over time in accordance with the principles of the present invention.

In accordance with a further aspect of the present invention, a patient's QT interval information can be monitored over time and trends in the QT interval displayed and reviewed. Since the effects of medication with some patients can be subtle with changes in the QT interval occurring very gradually, such a trend display can better reveal these subtle, long-term changes in the condition of the patient. FIG. 12 shows an example of a trend review display of the present invention. In this example the clinician has selected the display trends in QT changes by making this selection in menu box 140. The clinician has selected a four hour monitoring period for review in menu box 142. In display area 150 the clinician has chosen to display trends of the QTc and dQTc values over the four hour period by making this selection in menu box 144. In the display area 152 the clinician has chosen the display of the QT interval and the heart rate by making this selection in menu box 146. The display then shows the variations of these cardiac parameters over the previous four hour time period. Line 132 in the display is the trend line for dQTc, line 134 is the trend line for QTc, line 136 is the trend line for the heart rate, and line 138 is the trend line for the QT interval.

In the illustrated four hour time period, specific parameter values at specific moments are difficult to discern with precision. Accordingly, if the clinician sees a particular point on a trend line for which specific values are desired, the clinician slides the vertical cursor line 130 along the trend lines. In this example the cursor 130 is positioned at the time 13:00:00 in the displayed four hour period. The displays show the exact parameter values of the trend lines at the time position of the cursor 130 at the top of the display areas 150 and 152. For instance, in this example the values at the time position of the cursor 130 are QTc=436 msec., dQTc=20 msec., the QT interval is 360 msec, and the heart rate (QT-HR) is 88 beats per minute. Thus, the cursor 130 enables the clinician to zero in on precise moments of concern in the QT interval trending.

Figure 13:
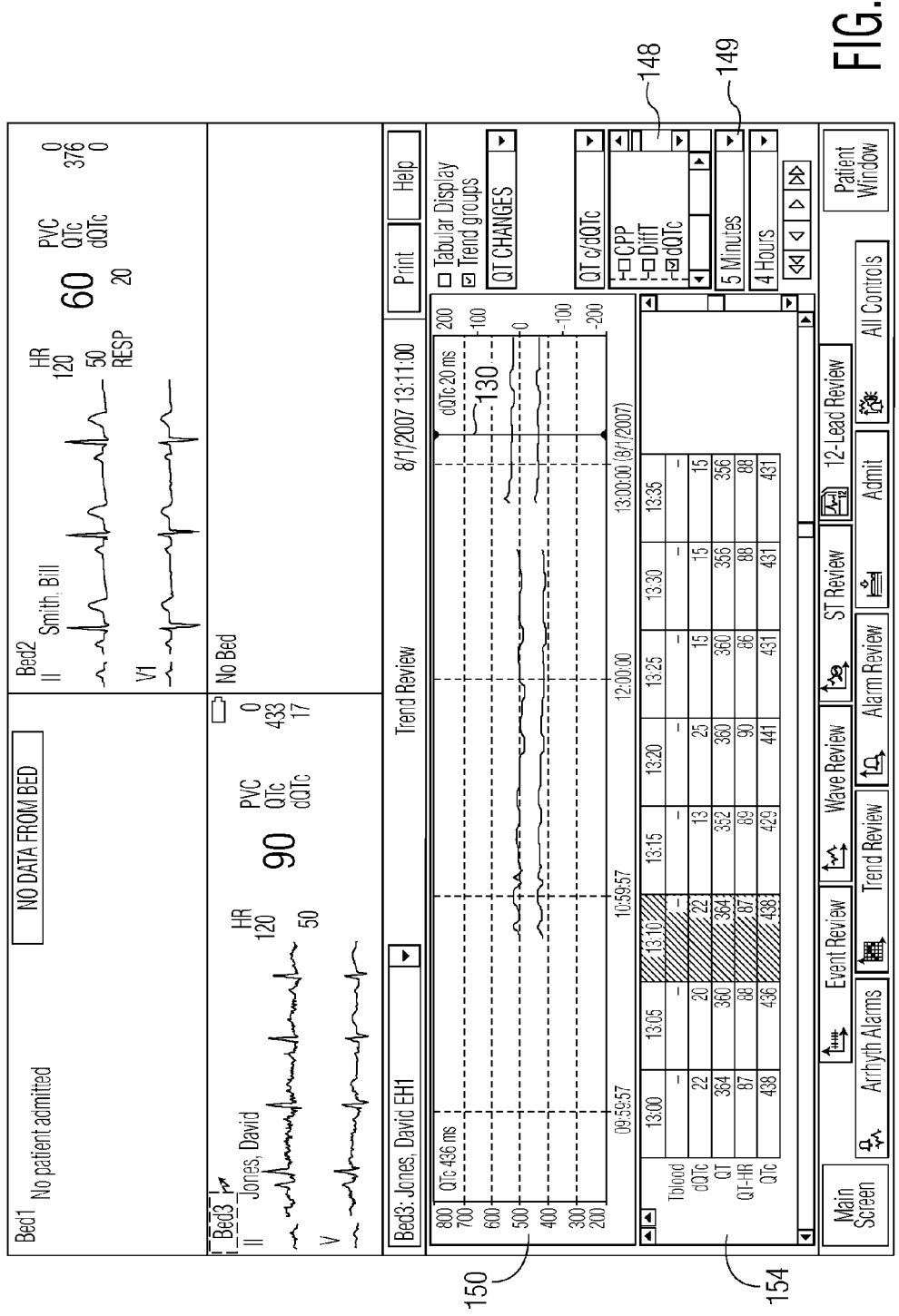
FIG. 13 illustrates a screen of a patient monitoring system displaying the trend of the QT interval both graphically and in tabular form.

FIG. 13 shows another variation in trend review in which the trends for QTc and dQTc are shown graphically in display area 150 and a number of QT parameters are shown in tabular form in display area 154. The parameter to be displayed are chosen by checking the desired parameters in box 148 and the measurement intervals for the tabular display are chosen from the pull down menu 149. In this example dQTc, QT, QT-HR and QTc are shown as recorded at five minute intervals starting at time 13:00. The time period of the tabular display is slightly shaded or colored in the graphical display area 150, and the QT parameter values at the time position of the cursor 130, when positioned as shown in this shaded or colored area, are highlighted at time 13:10 in the tabular display area 154. By this display technique the clinician can see not only the QT parameter values at the precise time of the position of cursor 130, but also quantized QT parameter values both before and after this time in the tabular display area.

Figure 14:
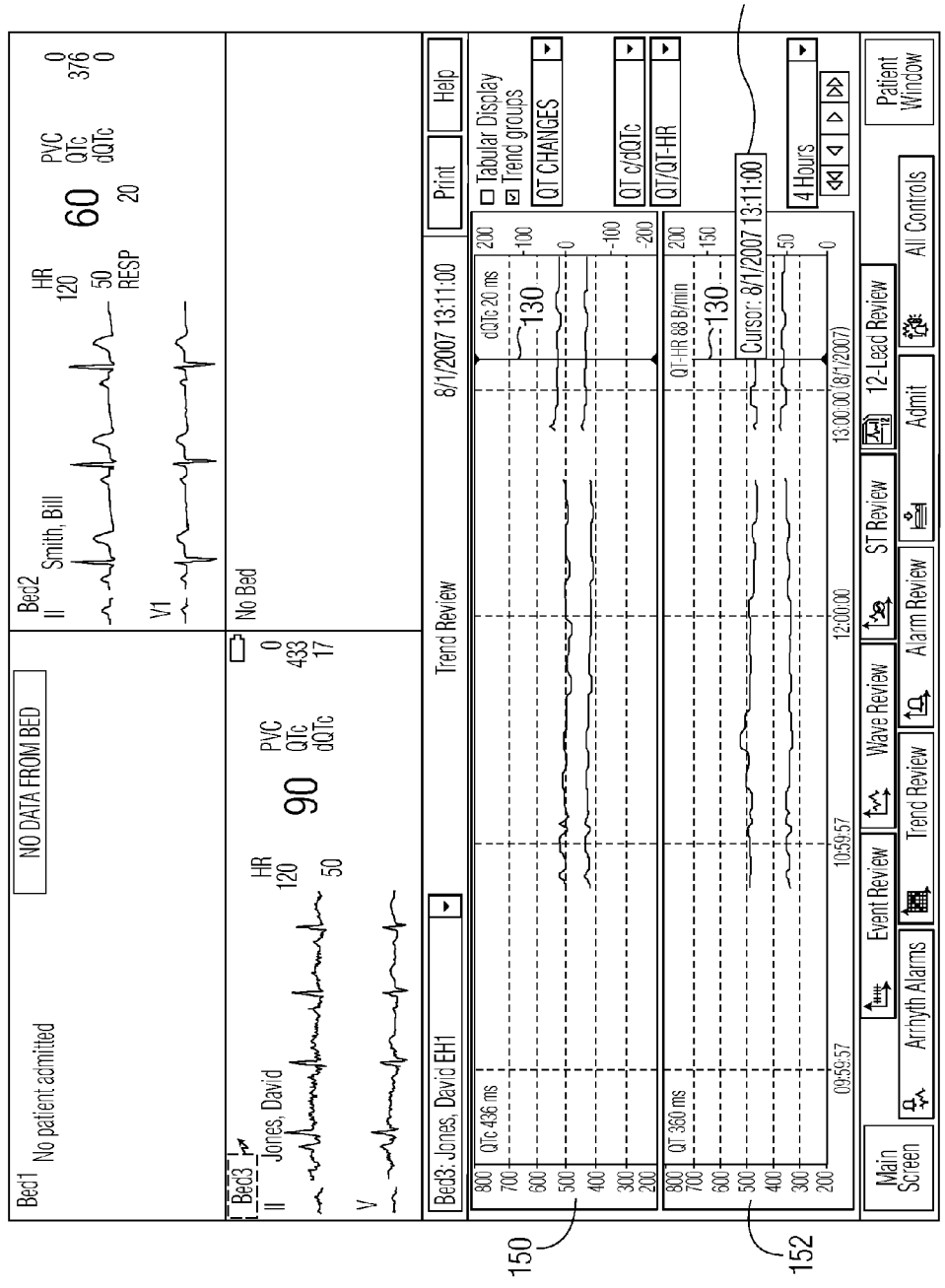
FIG. 14 illustrates a QT interval trending display with a popup showing the time at the cursor location.
Figure 15:
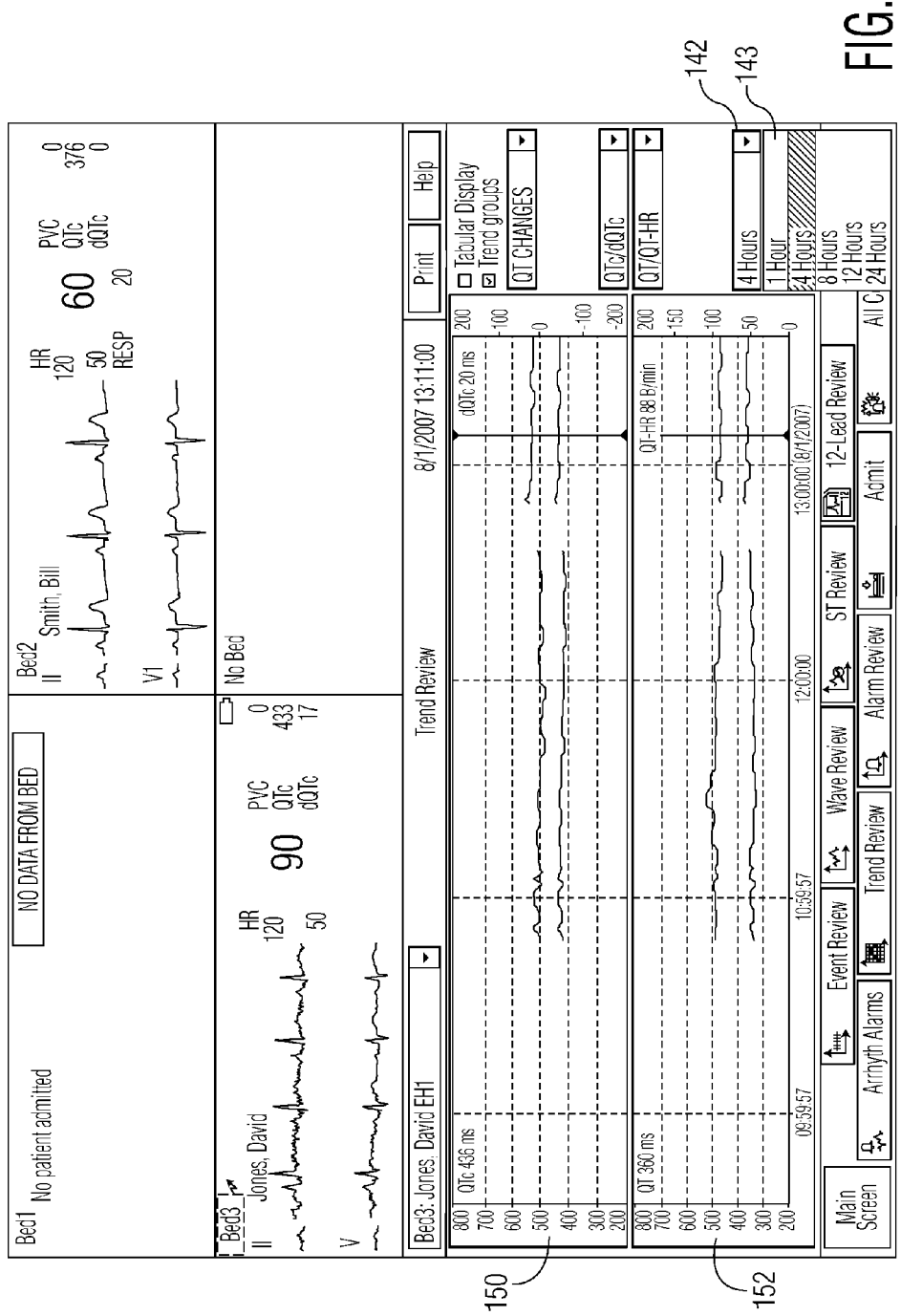
FIG. 15 illustrates a screen of a patient monitoring system displaying the time period selection box for the displayed trend of the QT interval in accordance with the present invention.

The graphical trend display of FIG. 14 is similar to that of FIG. 12, except that this example shows a popup time box 131 that appears whenever a user repositions the cursor 130. This popup time box enables the user to see the exact time position of the cursor 130 as it is moved over the four hour time window of the graphical trend display.

The graphical trend display of FIG. 14 is also similar to that of FIG. 12, except that this example shows the choices of a pull down menu 143 for the review period menu box 142. In this example the user has choices ranging from one hour to twenty-four hours for the displayed time period for reviewing trends of the QT parameters.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

What is claimed is:

1. An ECG system for monitoring QT interval information comprising:
    a source of ECG signal information;
    a QT interval processor responsive to ECG signal information which operates to periodically produce QT interval information;
    a storage device responsive to the QT interval processor which stores QT interval information as a function of time;
    a trend processor, responsive to QT interval information which operates to calculate a trend of QT information over a period of time, wherein the QT interval information which is trended further includes one or more of the QT interval, QTc values, and dQTc values;
    a QT interval correction processor which produces the QTc values corrected for a patient heart rate;
    a QT interval variation processor which produces dQTc values relative to a baseline QTc value;
    a display responsive to the trend processor and operable to display a trend of QT information over the period of time; and
    a user control operable to select the period of time over which the trend of QT information is displayed.

2. The ECG system of claim 1, wherein the display displays a variably settable alarm responsive to the QT interval information exceeding an alarm limit.

3. The ECG system according to claim 2, further including:
    an ECG strip recorder which automatically records an ECG strip around the time of the issuance of the alarm.

4. The ECG system according to claim 3, further including:
    a user operated alarm review display for recalling and displaying an ECG strip recorded around the time of the issuance of an alarm.

5. The ECG system according to claim 2, wherein the variably settable alarm has alarm limits for one or more of the QT interval information, QTc values, or dQTc values.

6. The ECG system of claim 1, wherein the display displays the trend of QT information graphically.

7. The ECG system of claim 6, further including:
    a user operable cursor which can be positioned over a graphical trend display, wherein the display is further responsive to the positioning of the cursor for displaying quantized values of QT information relating to the time position of the cursor.

8. The ECG system of claim 1, wherein the display displays the trend of QT information in tabular form.

9. The ECG system according to claim 1, further including:
    a user control operable for selecting one or more ECG leads which produce ECG signal information for the QT interval processor.

10. An ECG system for monitoring QT interval information, the system comprising:
    a display device;
    one or more processors programmed to:
        identify QT intervals in a received ECG signal over a plurality of cardiac cycles,
        calculate a QT trend line indicative of a change in the QT interval over a period of time,
        determine heart rates from the ECG signal,
        correct the identified QT intervals with the determined heart rates to generate corrected QT (QTc) intervals,
        calculate a QTc trend line indicative of a change in the corrected QT interval over the period of time,
        calculate a change in the corrected QT interval to generate a change in QTc (dQTc) intervals,
        calculate a dQTc trend line indicative of a change in the dQTc interval over the period of time,
        control the display device to display the ECG signal, QT trend line, QTc trend line, and dQTc trend line; and
    a user input device by which a user selects the period of time.

11. The ECG system of claim 10, wherein a cursor controlled by the user input device slides a vertical cursor line along the trend lines.

12. The ECG system of claim 11, wherein specific values along the trend lines are displayed in response to the position of the Cursor.

* * * * *